United States Patent
Yoshino et al.

(10) Patent No.: US 10,920,313 B2
(45) Date of Patent: Feb. 16, 2021

(54) DIAZADIENYL COMPOUND, RAW MATERIAL FOR FORMING THIN FILM, AND METHOD FOR MANUFACTURING THIN FILM

(71) Applicant: ADEKA CORPORATION, Tokyo (JP)

(72) Inventors: Tomoharu Yoshino, Tokyo (JP); Masaki Enzu, Tokyo (JP); Akihiro Nishida, Tokyo (JP); Atsushi Yamashita, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 157 days.

(21) Appl. No.: 16/326,973

(22) PCT Filed: Jul. 5, 2017

(86) PCT No.: PCT/JP2017/024662
§ 371 (c)(1),
(2) Date: Feb. 21, 2019

(87) PCT Pub. No.: WO2018/042871
PCT Pub. Date: Mar. 8, 2018

(65) Prior Publication Data
US 2019/0185994 A1    Jun. 20, 2019

(30) Foreign Application Priority Data

Aug. 29, 2016    (JP) .................. 2016-166588

(51) Int. Cl.
| | | |
|---|---|---|
| C23C 16/18 | (2006.01) | |
| C07C 251/08 | (2006.01) | |
| C07F 13/00 | (2006.01) | |
| C07F 15/04 | (2006.01) | |
| C23C 16/455 | (2006.01) | |

(52) U.S. Cl.
CPC ............ *C23C 16/18* (2013.01); *C07C 251/08* (2013.01); *C07F 13/005* (2013.01); (Continued)

(58) Field of Classification Search
None
See application file for complete search history.

(56) References Cited

U.S. PATENT DOCUMENTS

| | | | |
|---|---|---|---|
| 2013/0164456 A1 | 6/2013 | Winter et al. | |
| 2013/0251903 A1 | 9/2013 | Han | |
| 2015/0170961 A1* | 6/2015 | Romero | ............ H01L 21/76816 |
| | | | 438/641 |

FOREIGN PATENT DOCUMENTS

| | | |
|---|---|---|
| EP | 3 266 763 | 1/2018 |
| JP | 2013-545755 | 12/2013 |

(Continued)

OTHER PUBLICATIONS

International Search Report dated Sep. 26, 2017 in International (PCT) Application No. PCT/JP2017/024662.

(Continued)

*Primary Examiner* — Shamim Ahmed
*Assistant Examiner* — Bradford M Gates
(74) *Attorney, Agent, or Firm* — Wenderoth, Lind & Ponack, L.L.P.

(57) ABSTRACT

A diazadienyl compound represented by General Formula (I) below:

(Continued)

wherein $R^1$ represents a $C_{1-6}$ linear or branched alkyl group, and M represents nickel atom or manganese atom. In particular, since a compound in which $R^1$ in General Formula (I) is a methyl group has a high vapor pressure and a high thermal decomposition starting temperature, the compound is useful as a raw material for forming a thin film by a CVD method or ALD method.

4 Claims, 4 Drawing Sheets

(52) U.S. Cl.
CPC ...... *C07F 15/045* (2013.01); *C23C 16/45553* (2013.01); *C07F 15/04* (2013.01)

(56) References Cited

FOREIGN PATENT DOCUMENTS

| | | |
|---|---|---|
| JP | 6465699 | 2/2019 |
| WO | 2012/027357 | 3/2012 |
| WO | 2016/143456 | 9/2016 |

OTHER PUBLICATIONS

Extended European Search Report dated Feb. 27, 2020 in corresponding European Application No. 17845881.6.
Svoboda et al., "Bis(diazadien)metal(0)-complexes.III.Nickel(0)-bis(chelates) with aliphatic N-Substituents", Zeitschrift Fur Naturforschung—Section B Journal of Chemical Sciences, vol. 36, No. 7, Jul. 1, 1981, pp. 814-822.
Muresan et al., "Bis(α-diimine)nickel Complexes: Molecular and Electronic Structure of Three Members of the Electron-Transfer Series $[Ni(L)_2]^z$ (z=0, 1+, 2+) (L=2-Phenyl-1,4-bis(isopropyl)-1,4-diazabutadiene). A Combined Experimental and Theoretical Study", Inorganic Chemistry, vol. 46, No. 13, Jun. 1, 2007, pp. 5327-5337, XP55160423.
Notice of Reasons for Refusal dated Jun. 2, 2020 in corresponding Japanese Patent Application No. 2016-166588, with English-language translation.

\* cited by examiner

DIAZADIENYL COMPOUND, RAW MATERIAL FOR FORMING THIN FILM, AND METHOD FOR MANUFACTURING THIN FILM

TECHNICAL FIELD

The present invention relates to a novel diazadienyl compound, a raw material for forming a thin film that includes the compound, and a method for manufacturing a thin film by using the raw material for forming a thin film.

BACKGROUND ART

Thin-film materials including a metal element have been used for a variety of applications because such materials exhibit electric properties, optical properties and the like. For example, nickel and nickel-containing thin films are mainly used for parts of electronic components such as resistive films and barrier films, parts for recording media such as magnetic films, and parts for thin-film solar cells, such as electrodes.

Examples of methods for manufacturing such thin films include a sputtering method, an ion plating method, a MOD method such as a coating pyrolysis method and a sol-gel method, a CVD method and an atomic layer deposition method (referred to hereinbelow as an ALD method). The CVD and ALD methods are mainly used because they provide good quality thin films.

A large number of various materials have been reported as metal-supplying sources for use in the chemical vapor deposition method. For example, Patent Document 1 discloses a diazadienyl complex that can be used as a raw material for forming a thin film by an ALD method. Further, Patent Document 2 discloses a diazadiene-based metal compound that can be used in a chemical vapor deposition or atomic layer deposition. Patent Documents 1 and 2 do not specifically describe a diazadiene compound of the present invention.

Patent Document 1: U.S. Patent Application Publication No. 2013/0164456
Patent Document 2: Japanese Patent Application Laid-open No. 2013-545755

SUMMARY OF INVENTION

Technical Problem

When a metal-containing thin film is formed on a surface of a substrate by vaporizing a raw material for chemical vapor deposition, raw materials for chemical vapor deposition that has a high vapor pressure and no pyrophoricity and that can form a high quality thin film are preferred. In order to form higher quality thin film, it is necessary to perform heating at 200° C. or higher by using the ALD method. Therefore, a raw material for chemical vapor deposition that can be applied to the ALD method and that has a high vapor pressure, no pyrophoricity and a thermal decomposition starting temperature of 200° C. or higher has been required. Here, the high quality thin film means that a carbon content remained in the thin film is low.

Solution to the Problem

The present inventors have carried out investigations and discovered that the abovementioned problems can be solved by a specific diazadienyl compound, to achieve the present invention.

The present invention provides a diazadienyl compound represented by General Formula (I) below.

In the formula, $R^1$ represents a $C_{1-6}$ linear or branched alkyl group, and M represents nickel atom or manganese atom.

The present invention provides a raw material for forming a thin film that includes a diazadienyl compound represented by General Formula (I) above.

The present invention provides a method for manufacturing a thin film, comprising: introducing a vapor including a diazadienyl compound obtained by vaporizing the raw material for forming a thin film described above into a film formation chamber in which a substrate is disposed; and forming, on a surface of the substrate, a thin film including at least one atom selected from nickel atom and manganese atom by inducing decomposition and/or chemical reaction of the diazadienyl compound.

Advantageous Effects of the Invention

In accordance with the present invention, it is possible to obtain a diazadienyl compound having a high vapor pressure, no pyrophoricity and a very high thermal decomposition starting temperature. The diazadienyl compound is particularly suitable as a raw material for forming a thin film by a CVD method or an ALD method. A raw material for forming a thin film, comprising the diazadienyl compound, can form a high quality thin film having a low carbon content remained in the thin film by the CVD method or the ALD method. In particular, since the diazadienyl compound of the present invention has particularly good reactivity with hydrogen, the raw material for forming a thin film, comprising the diazadienyl compound, can form a very high quality nickel thin film by the ALD method.

DESCRIPTION OF EMBODIMENTS

The diazadienyl compound in accordance with the present invention is represent by General Formula (I) above. This compound is suitable as a precursor for a thin film manufacturing method having a vaporization step, such as the CVD method, and can be used for forming a thin film using the ALD method.

In General Formula (I) of the present invention, $R^1$ represents a $C_{1-6}$ linear or branched alkyl group, and M represents nickel atom or manganese atom.

Examples of the $C_{1-6}$ linear or branched alkyl group represented by $R^1$ include a methyl group, ethyl group, propyl group, isopropyl group, butyl group, isobutyl group, sec-butyl group, tert-butyl group, pentyl group, isopentyl group and hexyl group.

A compound in which $R^1$ in General Formula (I) is a methyl group is particularly preferred because the compound has a high vapor pressure and a high thermal decomposition starting temperature and a high quality thin film can be obtained when the compound is used as a raw material for forming a thin film by the CVD method or the ALD method. In methods for manufacturing thin films by MOD methods without a vaporization step, $R^1$ may be appropriately selected depending on the solubility in a solvent used, the thin film forming reaction and the like.

Preferred specific examples of the diazadienyl compound represented by General Formula (I) include the compounds represented by chemical formulas No. 1 to No. 12 below. In the chemical formulas No. 1 to No. 12, "Me" represents a methyl group, "Et" represents an ethyl group, "Pr" represents a propyl group, "iPr" represents an isopropyl group, "sBu" represents a sec-butyl group and "tBu" represents a tert-butyl group.

Compound No. 1

Compound No. 2

Compound No. 3

Compound No. 4

Compound No. 5

Compound No. 6

Compound No. 7

Compound No. 8

Compound No. 9

Compound No. 10

Compound No. 11

Compound No. 12

The diazadienyl compound of the present invention is not particularly restricted by the manufacturing method thereof and can be manufactured by using a well-known reaction. For example, a diazadienyl compound of nickel can be manufactured, for example, by a method of conducting a reaction of an inorganic nickel salt such as halide and nitrate, or a hydrate thereof with the corresponding diazadiene compound in the presence of a base such as sodium, lithium, sodium hydride, sodium amide, sodium hydroxide, sodium methylate, ammonia, and amine, or a method of conducting a reaction of an inorganic nickel salt such as halide and nitrate, or a hydrate thereof with a sodium complex, lithium complex, potassium complex or the like of the corresponding diazadiene compound.

In addition, the diazadiene compound used here is not particularly restricted by the manufacturing method thereof and can be manufactured by using a well-known reaction. For example, a diazadiene compound can be obtained by reacting an alkylamine and an alkylglyoxal in a solvent such as trichloromethane to obtain a product and extracting it with a suitable solvent, followed by dehydration treatment.

The raw material for forming a thin film of the present invention includes the diazadienyl compound of the present invention, which has been explained hereinabove, as a precursor for the thin film, and the form of the raw material differs depending on the manufacturing process in which the raw material for forming a thin film is to be used. For example, when a thin film including only at least one metal selected from nickel atom and manganese atom is manufactured, the raw material for forming a thin film of the present invention does not include metal compounds or semimetal compounds other than the diazadienyl compound. Meanwhile, where a thin film including metals and/or semimetals of two or more types is manufactured, the raw material for forming a thin film of the present invention includes, in addition to the abovementioned diazadienyl compound, a compound including the desired metal and/or a compound including the desired semimetal (can be also referred to hereinbelow as "other precursor"). As will be described hereinbelow, the raw material for forming a thin film of the present invention may additionally include an organic solvent and/or a nucleophilic reagent. Since physical properties of the diazadienyl compound serving as the precursor are advantageous for the CVD method and ALD method, the raw material for forming a thin film of the present invention is particularly useful as a raw material for chemical vapor deposition (referred to hereinbelow as "CVD").

Where the raw material for forming a thin film of the present invention is a raw material for chemical vapor deposition, the form thereof can be selected, as appropriate, according, e.g., to the delivery and feed method in the CVD method which is to be used.

The delivery and feed method can be a gas delivery method in which a CVD source is vaporized by heating and/or depressurizing the interior of a container in which the source is stored (can be referred to hereinbelow simply as "raw material container"), and the obtained vapor is introduced, optionally together with a carrier gas such as argon, nitrogen, and helium, into a film formation chamber in which a substrate is disposed (can be also referred to hereinbelow as "deposition reaction unit") or a liquid delivery method in which a CVD source is transported in a state of a liquid or solution into a vaporization chamber and vaporized by heating and/or depressurizing in the vaporization chamber, and the vapor is introduced into a film formation chamber. When the gas delivery method is used, the diazadienyl compound itself, which is represented by General Formula (I), can be used as the CVD source. When the liquid delivery method is used, the diazadienyl compound itself, which is represented by General Formula (I), or a solution obtained by dissolving the compound in an organic solvent can be used as the CVD source. Those CVD sources may additionally include the other precursor, a nucleophilic reagent or the like.

Further, CVD of a multicomponent system can be implemented by a method of vaporizing and feeding CVD sources for each component independently (can be also referred to hereinbelow as "single source method") and a method of vaporizing and feeding a mixed raw material obtained by mixing in advance multicomponent raw materials at the desired composition ratio (can be also referred to hereinbelow as "cocktail source method"). When the cocktail source method is used, a mixture of the diazadienyl compound of the present invention and the other precursor, or a mixed solution obtained by dissolving the mixture in an organic solvent can be used as the CVD source. The mixture or mixed solvent may additionally include a nucleophilic reagent.

The organic solvent is not particularly limited, and well-known typical organic solvents can be used. Examples of the organic solvents include acetates such as ethyl acetate, butyl acetate, and methoxyethyl acetate; ethers such as tetrahydrofuran, tetrahydropyran, ethylene glycol dimethyl ether, diethylene glycol dimethyl ether, triethylene glycol dimethyl ether, dibutyl ether, and dioxane; ketones such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons such as hexane, cyclohexane, methylcyclohexane, dimethylcyclohexane, ethylcyclohexane, heptane, octane, toluene, and xylene; hydrocarbons including a cyano group such as 1-cyanopropane, 1-cyanobutane, 1-cyanohexane, cyanocyclohexane, cycanobenzene, 1,3-dicyanopropane, 1,4-dicyanobutane, 1,6-dicyanohexane, 1,4-dicyanocyclohexane, and 1,4-dicyanobenzene; pyridine and lutidine. Such organic solvents are used individually or as mixed solvents of two or more thereof according to the relationship between the solute solubility, usage temperature, boiling point, and flash point. When such organic solvents are used, the amount of the entire precursor in the CVD source which is a solvent in which the precursor is dissolved in the organic solvent is preferably 0.01 mol/L to 2.0 mol/L, in particular, 0.05 mol/L to 1.0 mol/L. The amount of the entire precursor, as referred to herein, is the amount of the diazadienyl compound of the present invention when the raw material for forming a thin film of the present invention does not include a metal compound or a semimetal compound other than the diazadienyl compound of the present invention, and is the total amount of the diazadienyl compound of the present invention and the other precursor when the raw material for forming a thin film of the present invention includes a compound including other metal and/or a compound including a semimetal (the other precursor) in addition to the diazadienyl compound.

When CVD of a multicomponent system is performed, the other precursor which is used together with the diazadienyl compound of the present invention is not particularly limited, and any well-known typical precursor which has been used in CVD sources can be used.

Examples of the other precursor include one, or two or more compounds of silicon or a metal selected from a group including compounds having a hydride, a hydroxide, a halide, an azide, an alkyl, an alkenyl, a cycloalkyl, an aryl, an alkynyl, an amino, a dialkylaminoalkyl, a monoalkylamino, a dialkylamino, a diamine, a di(silyl-alkyl)amino, a di(alkyl-silyl)amino, a disilylamino, an alkoxy, an alkoxyalkyl, a hydrazido, a phosphido, a nitrile, a dialkylaminoalkoxy, an alkoxyalkyldialkylamino, a siloxy, a diketonate, a cyclopentadienyl, a silyl, a pyrazolate, a guanidinate, a phosphoguanidinate, an amidinate, a ketoiminate, a diketoiminate, a carbonyl, and a phosphoamidinate as a ligand.

Examples of metals for the precursor include magnesium, calcium, strontium, barium, radium, scandium, yttrium, titanium, zirconium, hafnium, vanadium, niobium, tantalum, chromium, molybdenum, tungsten, iron, osmium, cobalt, rhodium, iridium, palladium, platinum, copper, silver, gold, zinc, cadmium, aluminum, gallium, indium, germanium, tin, lead, antimony, bismuth, lanthanum, cerium, praseodymium, neodymium, promethium, samarium, europium, gadolinium, terbium, dysprosium, holmium, erbium, thulium, and ytterbium.

Such other precursors are well known in the pertinent technical field, and the manufacturing methods thereof are also well known. For example, where an alcohol compound is used as the organic ligand, the precursor can be manufactured by conducting a reaction of the abovementioned inorganic metal salt or a hydrate thereof and the alkali metal alkoxide of the alcohol compound. Examples of the inorganic metal salt and hydrate thereof include metal halides and nitrates, and examples of the alkali metal alkoxides include sodium alkoxide, lithium alkoxide, and potassium alkoxide.

In the case of a single source method, it is preferred that the other precursor be a compound demonstrating thermal and/or oxidative decomposition behavior similar to that of the diazadienyl compound of the present invention. In the case of a cocktail source method, it is preferred that the other precursor be a compound demonstrating similar thermal and/or oxidative decomposition behavior and further demonstrating no transformations induced by chemical reactions or the like at the time of mixing.

Compounds represented by Formulas (II-1) to (II-5) below are examples of precursors including titanium, zirconium, or hafnium among the other precursors.

(II-1)

(II-2)

(II-3)

(II-4)

(II-5)

In the formulas, $M^1$ represents titanium, zirconium, or hafnium; $R^a$ and $R^b$ each independently represent a $C_{1-20}$ alkyl group which may be substituted with a halogen atom and may contain an oxygen atom in a chain; $R^c$ represents a $C_{1-8}$ alkyl group; $R^d$ represents an optionally branched $C_{2-18}$ alkylene group; $R^e$ and $R^f$ each independently represent a hydrogen atom or a $C_{1-3}$ alkyl group; $R^g$, $R^h$, $R^k$, and $R^j$ each independently represent a hydrogen atom or a $C_{1-4}$ alkyl group; p represents an integer of 0 to 4; q represents 0 or 2; r represents an integer of 0 to 3; s represents an integer of 0 to 4; and t represents an integer of 1 to 4.

Examples of the $C_{1-20}$ alkyl group which may be substituted with a halogen atom and may contain an oxygen atom in a chain, this group being represented by $R^a$ and $R^b$ in Formulas (II-1) to (II-5), include a methyl group, ethyl group, propyl group, isopropyl group, butyl group, sec-butyl group, tert-butyl group, isobutyl group, pentyl group, isopentyl group, neopentyl group, tert-pentyl group, hexyl group, cyclohexyl group, 1-methylcyclohexyl group, heptyl group, 3-heptyl group, isoheptyl group, tert-heptyl group, n-octyl group, isooctyl group, tert-octyl group, 2-ethylhexyl group, trifluoromethyl group, perfluorohexyl group, 2-methoxyethyl group, 2-ethoxyethyl group, 2-butoxyethyl group, 2-(2-methoxyethoxy)ethyl group, 1-methoxy-1,1-dimethylmethyl group, 2-methoxy-1,1-dimethylethyl group, 2-ethoxy-1,1-dimethylethyl group, 2-isopropoxy-1,1-dimethylethyl group, 2-butoxy-1,1-dimethylethyl group, and 2-(2-methoxyethoxy)-1,1-dimethylethyl group. The $C_{1-8}$ alkyl group as represented by $R^c$ includes a methyl group, ethyl group, propyl group, isopropyl group, butyl group, sec-butyl group, tert-butyl group, isobutyl group, pentyl group, isopentyl group, neopentyl group, tert-pentyl group, hexyl group, 1-ethylpentyl group, cyclohexyl group, 1-methylcyclohexyl group, heptyl group, isoheptyl group, tert-heptyl group, n-octyl group, isooctyl group, tert-octyl group, and 2-ethylhexyl group. The optionally branched $C_{2-18}$ alkylene group which is represented by $R^d$ is a group derived from a glycol. Examples of the glycol include 1,2-ethanediol, 1,2-propanediol, 1,3-propanediol, 1,3-bu- tanediol, 2,4-hexanediol, 2,2-dimethyl-1,3-propanediol, 2,2-diethyl-1,3-propanediol, 2,2-diethyl-1,3-butanediol, 2-ethyl-2-butyl-1,3-propanediol, 2,4-pentanediol, 2-methyl-1,3-propanediol, and 1-methyl-2,4-pentanediol. Examples of the $C_{1-3}$ alkyl group which is represented by $R^e$ and $R^f$ include a methyl group, ethyl group, propyl group, and 2-propyl group. Examples of the $C_{1-4}$ alkyl group which is represented by $R^g$, $R^h$, $R^j$, and $R^k$ include a methyl group, ethyl group, propyl group, isopropyl group, butyl group, sec-butyl group, tert-butyl group, and isobutyl group.

Specific examples of precursors including titanium include tetrakis(alkoxy)titanium such as tetrakis(ethoxy)titanium, tetrakis(2-propoxy)titanium, tetrakis(butoxy)titanium, tetrakis(sec-butoxy)titanium, tetrakis(isobutoxy)titanium, tetrakis(tert-butoxy)titanium, tetrakis(tert-pentyl)titanium, and tetrakis(1-methoxy-2-methyl-2-propoxy)titanium; tetrakis-β-diketonatotitanium such as tetrakis(pentane-2,4-dionato)titanium, (2,6-dimethylheptane-3,5-dionato)titanium, and tetrakis(2,2,6,6-tetramethylheptane-3,5-dionato)titanium; bis(alkoxy)bis(β-diketonato)titanium such as bis(methoxy)bis(pentane-2,4-dionato)titanium, bis(ethoxy)bis(pentane-2,4-dionato)titanium, bis(tert-butoxy)bis(pentane-2,4-dionato)titanium, bis(methoxy)bis(2,6-dimethylheptane-3,5-dionato)titanium, bis(ethoxy)bis(2,6-dimethylheptane-3,5-dionato)titanium, bis(2-propoxy)bis(2,6-dimethylheptane-3,5-dionato)titanium, bis(tert-butoxy)bis(2,6-dimethylheptane-3,5-dionato)titanium, bis(tert-amyloxy)bis(2,6-dimethylheptane-3,5-dionato)titanium, bis(methoxy)bis(2,2,6,6-tetramethylheptane-3,5-dionato)titanium, bis(ethoxy)bis(2,2,6,6-tetramethylheptane-3,5-dionato)titanium, bis(2-propoxy)bis(2,6,6,6-tetramethylheptane-3,5-dionato)titanium, bis(tert-butoxy)bis(2,2,6,6-tetramethylheptane-3,5-dionato)titanium, and bis(tert-amyloxy)bis(2,2,6,6-tetramethylheptane-3,5-dionato)titanium; and glycoxybis(β-diketonato)titanium such as (2-methylpentanedioxy)bis(2,2,6,6-tetramethylheptane-3,5-dionato)titanium and (2-methylpentanedioxy)bis(2,6-dimethylheptane-3,5-dionato)titanium; (cyclopentadienyl)tris(dialkylamino)titanium such as (methylcyclopentadienyl)tris(dimethylamino)titanium, (ethylcyclopentadienyl)tris(dimethylamino)titanium, (cyclopentadienyl)tris(dimethylamino)titanium, (methylcyclopentadienyl)tris(ethylmethylamino)titanium, (ethylcyclopentadienyl)tris(ethylmethylamino)titanium, (cyclopentadienyl)tris(ethylmethylamino)titanium, (methylcyclopentadienyl)tris(diethylamino)titanium, (ethylcyclopentadienyl)tris(diethylamino)titanium, and (cyclopentadienyl)tris(diethylamino)titanium; (cyclopentadienyl)tris(alkoxy)titanium such as (cyclopentadienyl)tris(methoxy)titanium, (methylcyclopentadienyl)tris(methoxy)titanium, (ethylcyclopentadienyl)tris(methoxy)titanium, (propylcyclopentadienyl)tris(methoxy)titanium, (isopropylcyclopentadienyl)tris(methoxy)titanium, (butylcyclopentadienyl)tris(methoxy)titanium, (isobutylcyclopentadienyl)tris(methoxy)titanium, (tert-butylcyclopentadienyl)tris(methoxy)titanium, and (pentamethylcyclopentadienyl)tris(methoxy)titanium.

Examples of precursors including zirconium or hafnium are compounds presented as examples of titanium-containing precursors in which titanium is substituted with zirconium or hafnium.

Examples of precursors including rare earth metals are compounds represented by Formulas (III-1) to (III-3).

In the formulas, $M^2$ represents a rare earth atom; $R^a$ and $R^b$ each independently represent a $C_{1-20}$ alkyl group which may be substituted with a halogen atom and may contain an oxygen atom in a chain; $R^c$ represents a $C_{1-8}$ alkyl group; $R^e$ and $R^f$ each independently represent a hydrogen atom or a $C_{1-3}$ alkyl group; $R^g$ and $R^j$ each independently represent a $C_{1-4}$ alkyl group; p' represents an integer of 0 to 3; and r' represents an integer of 0 to 2.

Examples of rare earth atoms represented by $M^2$ in the precursor including a rare earth element include scandium, yttrium, lanthanum, cerium, praseodymium, neodymium, promethium, samarium, europium, gadolinium, terbium, dysprosium, holmium, erbium, thulium, ytterbium, and lutetium. Examples of groups represented by $R^a$, $R^b$, $R^c$, $R^e$, $R^f$, $R^g$, and $R^j$ include groups presented by way of examples with respect to the titanium-containing precursors.

If necessary, the raw material for forming a thin film of the present invention may include a nucleophilic reagent to stabilize the diazadienyl compound of the present invention and the other precursor. Examples of the nucleophilic reagent include ethylene glycol ethers such as glyme, diglyme, triglyme, and tetraglyme; crown ethers such as 18-crown-6, dicyclohexyl-18-crown-6,24-crown-8, dicyclohexyl-24-crown-8, and dibenzo-24-crown-8; polyamines such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyltriethylenetetramine, and triethoxytriethyleneamine; cyclic polyamines such as cyclam and cyclen; heterocyclic compounds such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane; β-keto esters such as methyl acetoacetate, ethyl acetoacetate, and 2-methoxyethyl acetoacetate; and β-diketones such as acetylacetone, 2,4-hexanedione, 2,4-heptanedione, 3,5-heptanedione, and dipivaroylmethane. These nucleophilic reagents are used in an amount preferably within a range of 0.1 mol to 10 mol, more preferably 1 mol to 4 mol per mole of the amount of the entire precursor.

In the raw material for forming a thin film of the present invention, the amount of metal element impurities, halogen impurities such as chlorine-containing impurities, and organic impurities, which are different from the components constituting the raw materials, needs to be minimized. The content of the metal element impurities is preferably 100 ppb or less, and more preferably 10 ppb or less for each element, and the total amount of the impurities is preferably 1 ppm or less, and more preferably 100 ppb or less. In particular, when the raw material is used to form a gate insulating layer, a gate film, or a barrier layer of an LSI, it is necessary to reduce the amount of alkali metal elements and alkaline earth metal elements which affect the electric properties of a thin film to be obtained. The amount of the halogen impurities is preferably 100 ppm or less, more preferably 10 ppm or less, and most preferably 1 ppm or less. The total amount of organic impurities is preferably 500 ppm or less, more preferably 50 ppm or less, and most preferably 10 ppm or less. Since moisture causes particle generation in the raw material for chemical vapor deposition or particle generation during thin film formation, it is better to remove moisture as much as possible prior to use from the precursor, the organic solvent, and the nucleophilic reagent in order to reduce the amount of moisture therein. The amount of moisture in each of the precursor, the organic solvent, and the nucleophilic reagent is 10 ppm or less, and more preferably 1 ppm or less.

Further, in order to reduce or prevent the particle contamination of the thin film to be formed, it is preferred that the raw material for forming a thin film of the present invention include as few particles as possible. More specifically, in particle measurements with a particle detector of a light scattering type in a liquid phase, the number of particles larger than 0.3 µm is preferably 100 or less in 1 ml of the liquid phase, more preferably the number of particles larger than 0.2 µm is 1000 or less in 1 ml of the liquid phase, and most preferably the number of particles larger than 0.2 µm is 100 or less in 1 ml of the liquid phase.

A method for manufacturing a thin film of the present invention by which a thin film is manufactured by using the raw material for forming a thin film of the present invention is based on the CVD method in which a vapor produced by vaporizing the raw material for forming a thin film of the present invention, and an optionally used reactive gas are introduced into a film formation chamber in which a substrate is disposed, and the precursor is then decomposed and/or chemically reacted on the substrate to grow and deposit a thin film including a metal on the substrate surface. The method for delivering and feeding the raw materials, the deposition method, manufacturing conditions, and manufacturing apparatus are not particularly restricted, and well-known typical conditions and methods can be used.

Examples of the optionally used reactive gas include oxidative gases such as oxygen, ozone, nitrogen dioxide, nitrogen monoxide, water vapor, hydrogen peroxide, formic acid, acetic acid, and acetic anhydride; reductive gases such as hydrogen; and gases producing nitrides, for example, organic amine compounds such as monoalkylamines, dialkylamines, trialkylamines, and alkylenediamines, hydrazine, and ammonia. These gases can be used individually or in combinations of two or more thereof. In particular, since the diazadienyl compound of the present invention has particularly good reactivity with hydrogen, the diazadienyl compound can form a very high quality nickel thin film by the ALD method using hydrogen as a reactive gas.

Examples of the delivery and feeding methods include the above-described gas delivery method, liquid delivery method, single source method, and cocktail source method.

Examples of the deposition method include thermal CVD in which a source gas or a source gas and a reactive gas are reacted only by heat in order to deposit a thin film; plasma CVD in which heat and plasma are used; photo-excited CVD in which heat and light are used; photo- and plasma-excited CVD in which heat, light and plasma are used; and ALD in which the CVD deposition reaction is separated into elementary steps and deposition is performed step by step at a molecular level.

Examples of the substrate material include silicon, ceramics such as silicon nitride, titanium nitride, tantalum nitride, titanium oxide, titanium nitride ruthenium oxide, zirconium oxide, hafnium oxide, and lanthanum oxide; glass; and metals such as metallic ruthenium. The substrate may be in the form of a sheet, sphere, fibers, and flakes. The substrate surface may be flat or may have a three-dimensional structure such as a trench structure.

The manufacturing conditions include the reaction temperature (substrate temperature), reaction pressure, deposition rate, and the like. The reaction temperature is preferably 150° C. or higher, more preferably 150° C. to 400° C. and particularly preferably 200° C. to 350° C., at which the diazadienyl compound of the present invention is sufficiently reactive. The reaction pressure is preferably from atmospheric pressure to 10 Pa for thermal CVD and photo-excited CVD, and preferably from 2000 Pa to 10 Pa when plasma is used.

The deposition rate can be controlled by the raw material feed conditions (vaporization temperature and vaporization pressure), reaction temperature, and reaction pressure. Since a high deposition rate can degrade the properties of the resulting thin film and a low deposition rate can cause problems with productivity, the deposition rate is preferably 0.01 nm/min to 100 nm/min and more preferably 1 nm/min to 50 nm/min. In the ALD method, the control is performed by the number of cycles so as to obtain the desired film thickness.

The temperature or pressure during vaporization of the raw material for forming a thin film can be also considered as the manufacturing condition. The step of obtaining the vapor by vaporizing the raw material for forming a thin film may be performed inside the raw material container or inside the vaporization chamber. In either case, it is preferred that the raw material for forming a thin film of the present invention be evaporated at 0° C. to 150° C. Further, where the raw material for forming a thin film is vaporized to obtain the vapor inside the raw material container or vaporization chamber, it is preferred that the pressure inside the raw material container and the pressure inside the vaporization chamber be 1 Pa to 10,000 Pa.

The method for manufacturing a thin film of the present invention, when it is realized by the ALD method, may include a raw material introduction step in which the raw material for forming a thin film is vaporized to obtain a vapor and the vapor is introduced into the film formation chamber by the abovementioned delivery and feeding method, and also a precursor thin film formation step of forming a precursor thin film on the surface of the substrate with the diazadienyl compound in the vapor, an evacuation step of evacuating the unreacted diazadienyl compound gas, and a metal-containing thin film formation step of chemically reacting the precursor thin film with a reactive gas and forming a thin film including the metal on the surface of the substrate.

Each of the abovementioned steps will be described hereinbelow in greater detail. When a metal thin film including at least one atom selected from nickel atom and manganese atom is famed by the ALD method, initially, the raw material introduction step, which has been explained hereinabove, is performed. The temperature and pressure preferred when vaporizing the raw material for forming a thin film are the same as explained hereinabove. Then, a precursor thin film is formed on the substrate surface with the diazadienyl compound introduced in the deposition reaction unit (precursor thin film formation step). At this time, heat may be applied by heating the substrate or heating the deposition reaction unit. The precursor thin film which is formed in this step is a thin film generated by decomposition and/or reaction of part of the diazadienyl compound and has a composition different from the target metal thin film. The substrate temperature employed in this step is preferably from room temperature to 500° C., more preferably from 150° C. to 350° C. The pressure in the system (in the film formation chamber) when this step is performed is preferably 1 Pa to 10,000 Pa, more preferably 10 Pa to 1000 Pa.

The unreacted diazadienyl compound gas and byproduct gas are then evacuated from the deposition reaction unit (evacuation step). The unreacted diazadienyl compound gas and byproduct gas are ideally completely evacuated from the deposition reaction unit, but such complete evacuation is not always necessary. Examples of the evacuation method include a method of purging the interior of the system with an inactive gas such as nitrogen, helium, and argon, a method of evacuating by depressurizing the interior of the system, and a method in which the aforementioned methods are combined. The degree of depressurization when the depressurization method is used is preferably 0.01 Pa to 300 Pa, more preferably 0.01 Pa to 100 Pa.

The reactive gas is then introduced into the deposition reaction unit and the target metal thin film is formed from the precursor thin film, which has been formed in the preceding precursor thin film formation step, under the action of the reactive gas or the action of the reactive gas and heat (metal thin film formation step). The temperature when heat is used in this step is preferably from room temperature to 500° C., more preferably from 150° C. to 350° C. The pressure in the system (in the film formation chamber) in which this step is performed is preferably 1 Pa to 10,000 Pa, more preferably 10 Pa to 1000 Pa. Since the diazadienyl compound of the present invention has good reactivity with reactive gases, a high quality thin film having a low carbon content can be obtained.

When the ALD method is used in the above-described manner in the method for manufacturing a thin film of the present invention, thin film deposition performed by a series of operations including the raw material introduction step, precursor thin film formation step, evacuation step, and metal thin film formation step may be taken as one cycle, and such cycles may be repeated a plurality of times till a thin film of a necessary thickness is obtained. In this case, after one cycle is completed, it is preferred that the unreacted diazadienyl compound gas, reactive gas, and byproduct gas be evacuated from the deposition reaction unit in the same manner as in the evacuation step, and the next cycle be thereafter performed.

When a thin film is formed by the ALD method, energy such as plasma, light, and voltage may be applied, and a catalyst may be used. The time period for applying the energy and the time period for using the catalyst are not particularly limited. For example, the energy may be applied and the catalyst may be used when the diazadienyl compound gas is introduced in the raw material introduction step, during heating in the precursor thin film formation step or thin film formation step, during evacuation of the interior of the system in the evacuation step, when the reactive gas is introduced in the thin film formation step, and also between the aforementioned steps.

Further, in the method for manufacturing a thin film of the present invention, annealing may be performed under an inactive gas atmosphere, an oxidizing atmosphere, or a reducing atmosphere after the thin film deposition to obtain better electric properties, and a reflow step may be employed when bump embedding is needed. In this case, the temperature is 200° C. to 1000° C., preferably 250° C. to 500° C.

Figure 1:
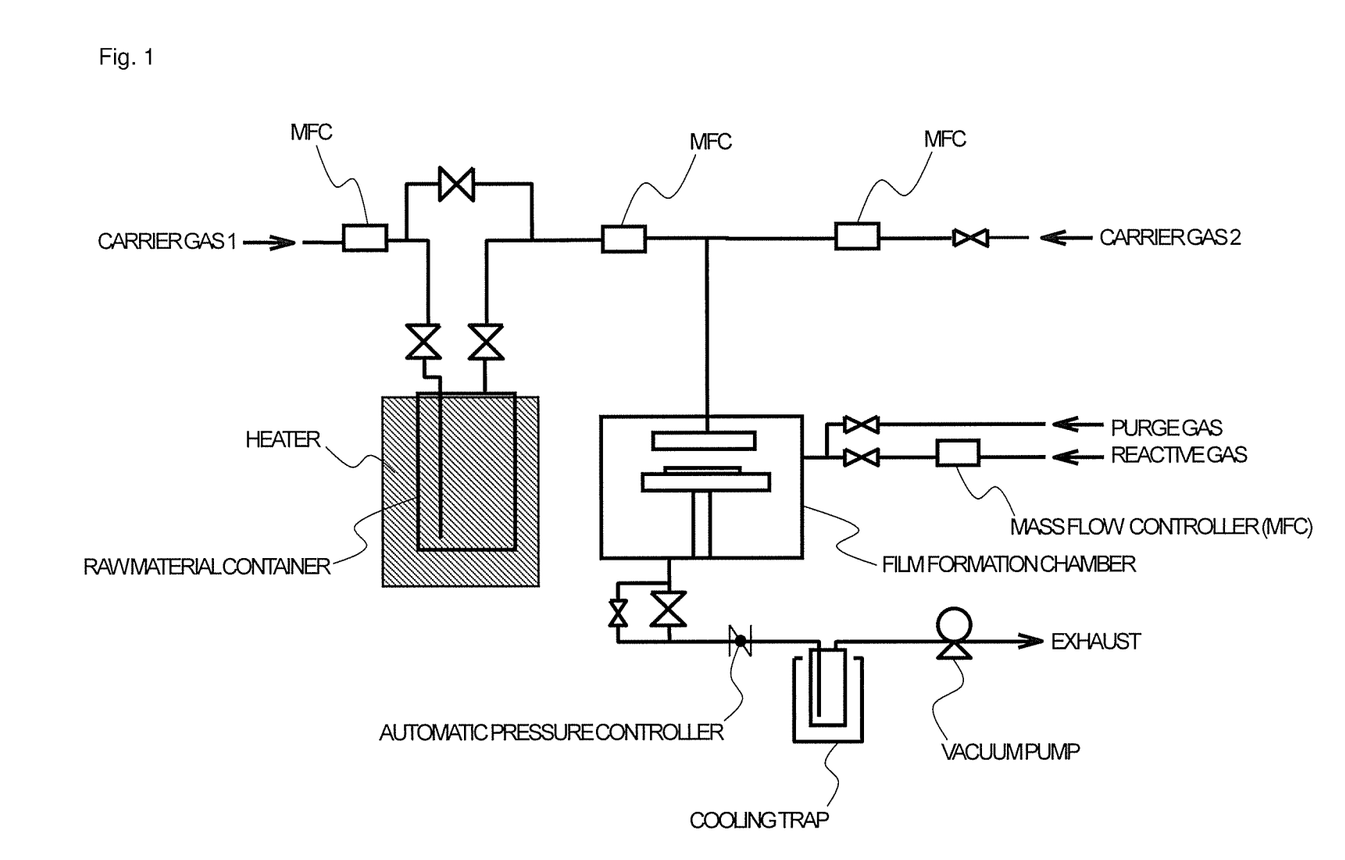
FIG. 1 is a conceptual diagram illustrating an example of a chemical vapor deposition apparatus for use in the method for manufacturing a thin film in the present invention.
Figure 2:
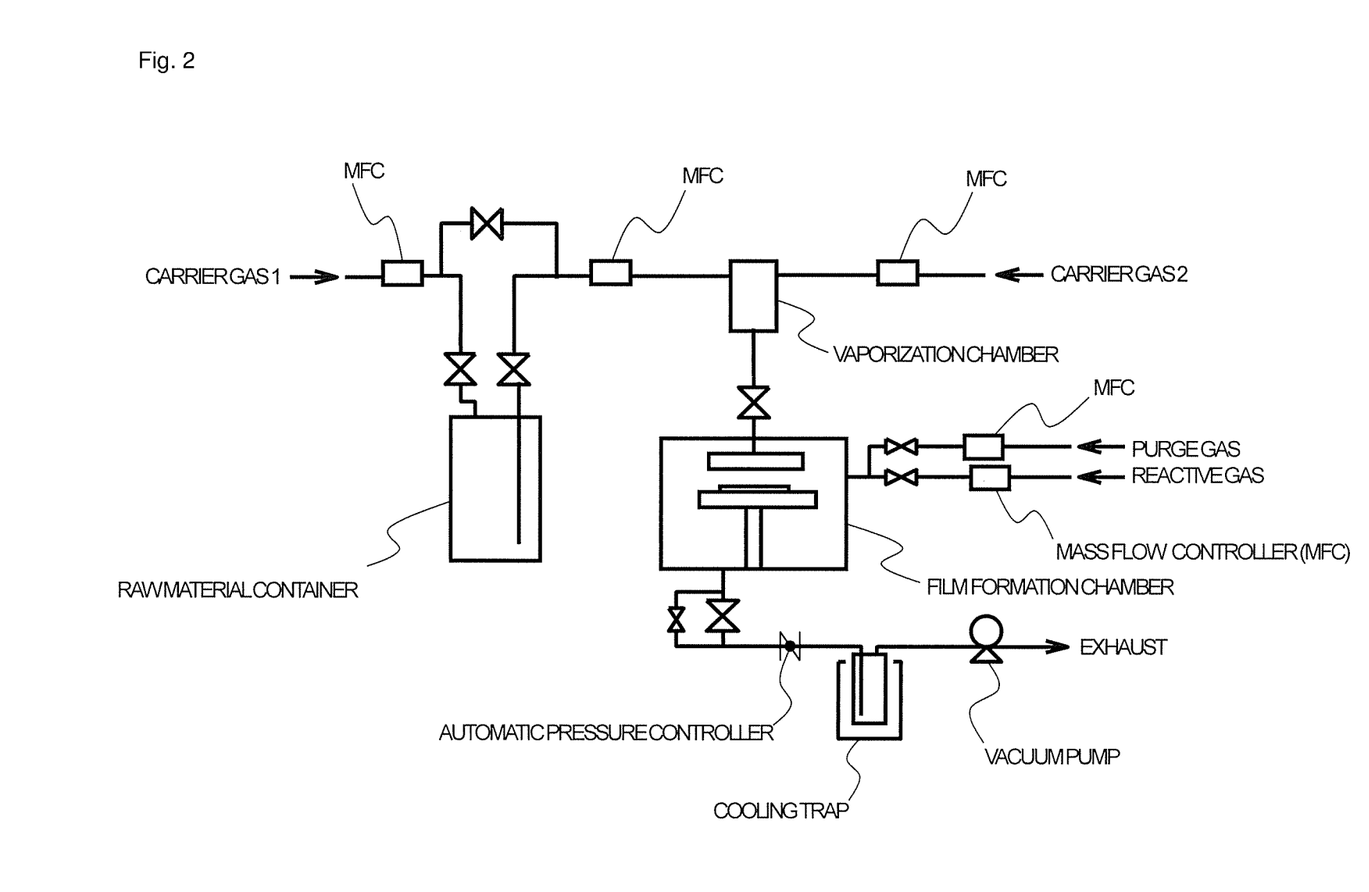
FIG. 2 is a conceptual diagram illustrating another example of a chemical vapor deposition apparatus for use in the method for manufacturing a thin film in the present invention.
Figure 3:
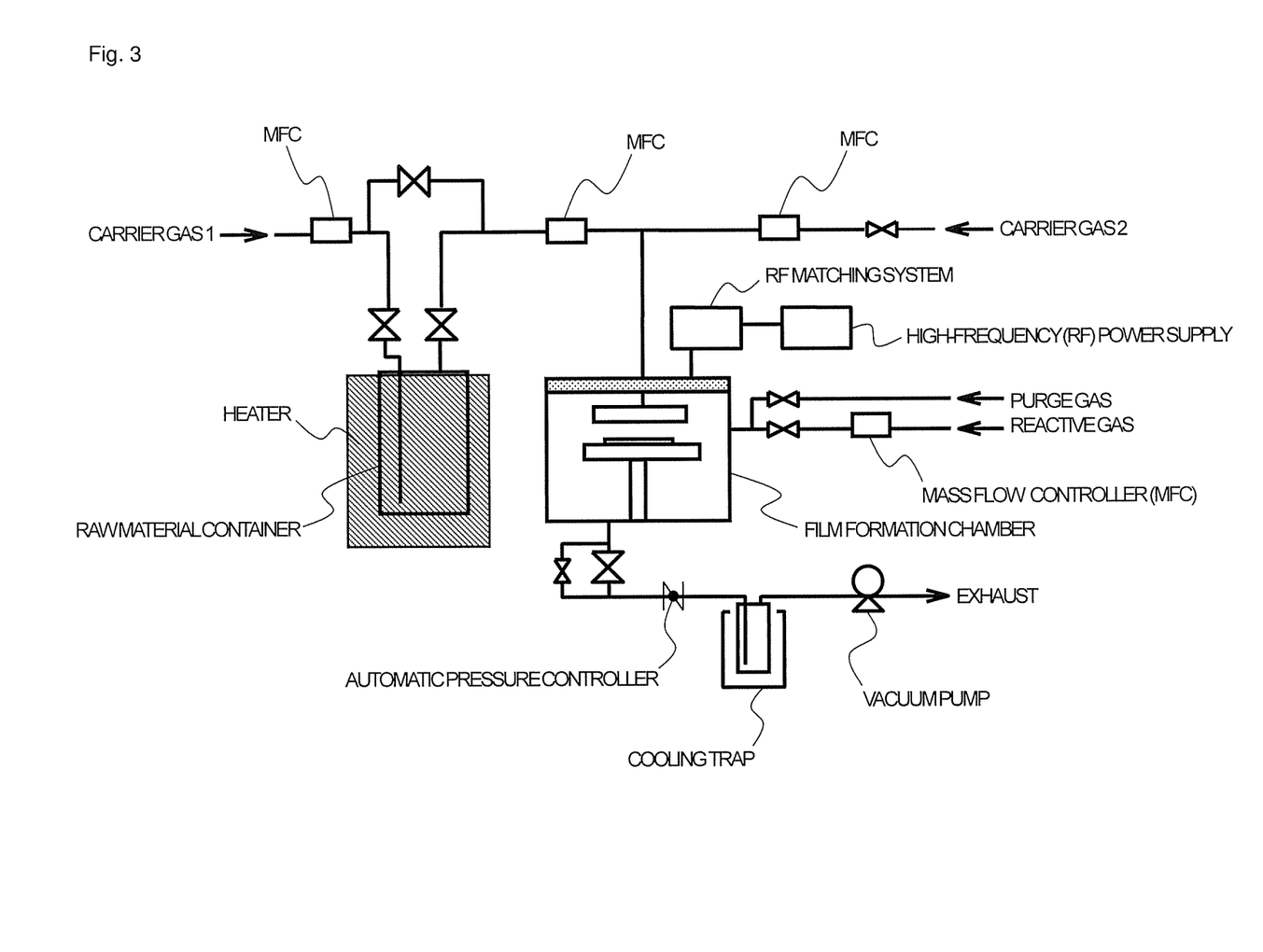
FIG. 3 is a conceptual diagram illustrating another example of a chemical vapor deposition apparatus for use in the method for manufacturing a thin film in the present invention.
Figure 4:
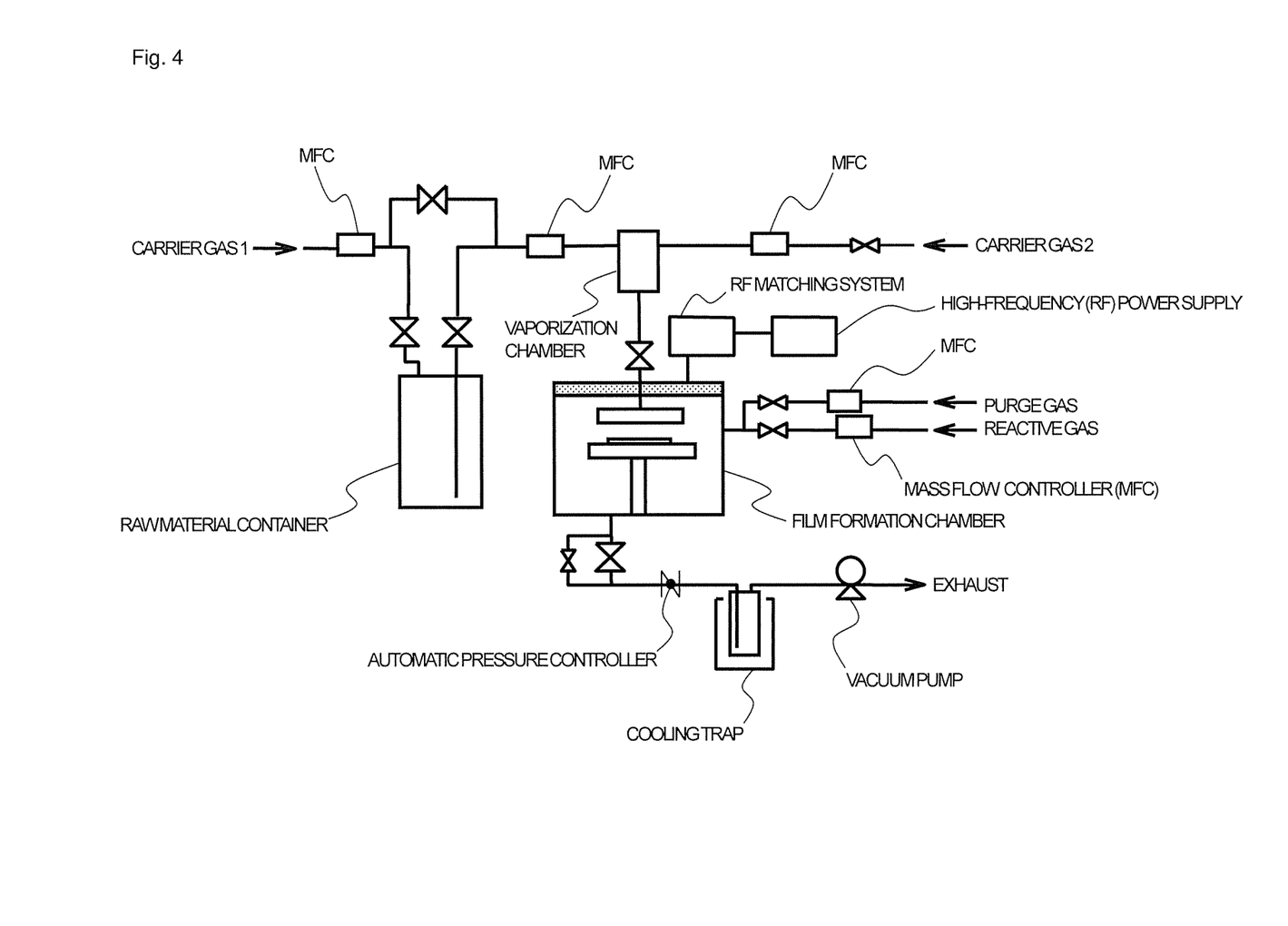
FIG. 4 is a conceptual diagram illustrating another example of a chemical vapor deposition apparatus for use in the method for manufacturing a thin film in the present invention.

A well-known chemical vapor deposition apparatus can be used for manufacturing a thin film by using the raw material for forming a thin film of the present invention. Specific examples of suitable apparatuses include an apparatus, such as depicted in FIG. 1, in which a precursor can be fed by bubbling, and an apparatus, such as depicted in FIG. 2, which has a vaporization chamber. An apparatus can be also used in which, as depicted in FIG. 3 and FIG. 4, plasma treatment can be performed with respect to a reactive gas. The single-substrate apparatuses, such as depicted in FIG. 1 to FIG. 4, are not limiting, and an apparatus which uses a batch furnace and is capable of simultaneous processing of a large number of substrates can be also used.

Where a thin film is manufactured using the raw material for forming a thin film of the present invention, the desired type of thin film such as metal, oxide ceramic, nitride ceramic, and glass can be formed by appropriately selecting the other precursor, reactive gas, and manufacturing conditions. Such thin films are known to exhibit various electric properties, optical properties and the like, and are used for a variety of applications. For example, copper and copper-containing thin films have been used as wiring materials for LSI because of a high electric conductivity, high resistance to electromigration, and a high melting point. Further, nickel and nickel-containing thin films are mainly used for parts of electronic components such as resistive films and barrier films, parts for recording media such as magnetic films, and parts for thin-film solar cells, such as electrodes.

EXAMPLES

The present invention will be explained hereinbelow in greater detail with reference to Examples and Evaluation Examples. However, the present invention is not limited by the Examples, etc., below.

[Manufacture Example 1] Manufacture of N, N'-diisopropyl-propane-1,2-diimine 197 g (3.33 mol) of isopropylamine and 496 g (4.16 mol) of dehydrated trichloromethane were loaded into a 1 L 4-necked flask and cooled to about 10° C. 150 g (0.833 mol) of a 40% pyruvaldehyde aqueous solution was added dropwise to this solution for 1 hour so that a liquid temperature was 10° C. to 14° C. After the end of the dropping, the mixture was stirred at a liquid temperature of 10° C. for 2 hours. Thereafter, the reaction solution was allowed to stand and the organic layer was separated. Further, the aqueous layer was extracted twice with trichloromethane (100 g), and the organic layer was recovered. All the organic layers were combined, dehydrated with sodium sulfate and filtered, and the solvent was removed at an oil bath temperature of 60° C. to 70° C. under a slightly reduced pressure. Thereafter, distillation was performed at an oil bath temperature of 64° C. under a reduced pressure. The obtained fraction was a pale yellow transparent liquid. The yield was 95.5 g and the percentage yield was 74.0%.

(Analytical Data)
(1) Mass spectrometry m/z: 154 (M+)
(2) Elemental analysis C: 72.2 mass %, H: 12.0 mass %, N: 17.9 mass % (theoretical values; C: 70.0 mass %, H: 11.8 mass %, N: 18.2 mass %)

[Example 1] Manufacture of Compound No. 1

21.4 g (138.9 mmol) of N, N'-diisopropyl-propane-1,2-diimine obtained above and dehydrated tetrahydrofuran (412 g) were loaded into a 1 L 4-necked flask and cooled to −30° C. with a dry ice/IPA bath. 0.988 g (142.4 mmol) of metallic lithium pieces was gradually added thereto and reacted at −10° C. This solution was added dropwise to a suspension of 9.0 g (69.45 mmol) of nickel chloride and dehydrated tetrahydrofuran (412 g) at about −10° C., and the temperature was raised to room temperature and then reacted for 15 hours. Thereafter, a solvent was removed at an oil bath temperature of 65° C. under a slightly reduced pressure. After allowing it to cool, dehydrated hexane was added to dissolve the product, followed by filtration through a membrane filter. The solvent was removed from the resulting filtrate at an oil bath temperature of 65° C. under a slightly reduced pressure and the residue was dried. The obtained residue was subjected to distillation at an oil bath temperature of 115° C. and a pressure of 20 Pa to obtain a reddish black viscous liquid target product. The yield was 5.8 g, and the percentage yield was 20.5%. Spontaneous combustion was checked with respect to the obtained target product by allowing the product to stay in the air. There was no spontaneous combustion.
(Analytical Data)
(1) $^1$H-NMR (solvent: heavy benzene) (chemical shift: multiplicity:H number)
(8.976:s:1) (3.151-3.087:m:1) (2.651-2.587:m:1) (1.937-1.870:m:12) (−1.408:s:3)
(2) Elemental analysis (metal analysis: ICP-AES, chlorine analysis: TOX)
Ni: 15.9 mass %, C: 58.6 mass %, H: 10.0 mass %, N: 15.5 mass % (theoretical values: Ni: 16.0 mass %, C: 58.8 mass %, H: 9.88 mass %, N: 15.3 mass %), Chlorine (TOX): less than 10 ppm

[Evaluation Example 1] Evaluation of Physical Properties of Compounds

The states of Compound No. 1 and Comparative Compound 1 shown below at normal pressure, 30° C. were each visually observed. The temperatures at which the thermal decompositions of Compound No. 1 and Comparative Compound 1 shown below started were measured by DSC. The temperatures at which the weights of Compound No. 1 and Comparative Compound 1 shown below were reduced by 50% under a reduced pressure were measured by TG-DTA. The results are shown in Table 1.
(Reduced Pressure TG-DTA Measurement Conditions)
10 Torr, Ar flow: 50 ml/min, Heating rate: 10° C./min, sample amount: about 10 mg Comparative Compound 1

TABLE 1

| Compound | State | Thermal decomposition starting temperature (° C.) | Reduced pressure TG-DTA 50% mass reduction temperature (° C.) |
|---|---|---|---|
| Evaluation Example 1-1 | Compound No. 1 | Liquid | 245 | 142.8 |
| Evaluation Example 1-2 | Comparative Compound 1 | Liquid | 230 | 133.8 |

It can be seen from Table 1 above that Compound No. 1 and Comparative Compound 1 are compounds that are liquid under conditions of normal pressure, 30° C., and have a thermal decomposition starting temperature of 200° C. or higher. It can be seen that Compound No. 1 has a thermal decomposition starting temperature about 15° C. higher than Comparative Compound 1. Further, the reduced pressure TG-DTA results show that Compound No. 1 has a sufficient vapor pressure as a raw material for chemical vapor deposition although Compound No. 1 has a slightly higher 50% mass reduction temperatures than Comparative Compound 1.

[Example 2] Manufacture of Metal Nickel Thin Films by ALD Method

Metal nickel thin film was manufactured on Cu substrates by ALD method under the following conditions using Compound No. 1 as a raw material for chemical vapor deposition, using the chemical vapor deposition apparatus shown in FIG. 1. Regarding the obtained thin film, the film thickness was measured by the X-ray reflectivity method and the thin film structure and composition were confirmed by X-ray analysis and X-ray photoelectron spectroscopy. The film thickness was 7 to 8 nm, the film was composed of metal nickel (confirmed from Ni2p peak in XPS analysis), and the carbon content remained in the thin film was below the detection limit of 0.1 atom %. The film thickness obtained per cycle was about 0.05 nm.
(Conditions)
Reaction temperature (substrate temperature): 250° C., reactive gas: hydrogen gas
(Steps)
150 cycles were performed, with each cycle consisting of the series of steps shown in (1) to (4) below:
(1) Vapor from chemical vapor deposition material that has been vaporized at a material container heating temperature of 100° C. and a material container internal pressure of 100 Pa is introduced into film formation chamber, and deposited for 30 seconds at a system pressure of 100 Pa;
(2) Unreacted material and byproduct gas are removed by 5 seconds of argon purging;
(3) Reactive gas is introduced into film formation chamber, and reacted for 30 seconds at a system pressure of 100 Pa;
(4) Unreacted material and byproduct gas are removed by 5 seconds of argon purging.

Comparative Example 1

A metal nickel thin film was manufactured in a manner similar to Example 2, except that Comparative Compound 1 above was used as a raw material for chemical vapor deposition. Regarding the obtained thin film, the film thickness was measured by the X-ray reflectivity method and the thin film structure and composition were confirmed by X-ray analysis and X-ray photoelectron spectroscopy. The film thickness was 6 nm, the film was composed of metal nickel (confirmed from Ni2p peak in XPS analysis), and the carbon content remained in the thin film was 24 atom %. The film thickness obtained per cycle was 0.04 nm.

It was found from the results above that Example 2 could manufacture a very high quality metal nickel thin film having a low carbon content remained in the thin film by ALD method. On the other hand, it was found that Comparative Example 1 could not manufacture a good quality metal nickel thin film since many carbon components remained in the metal nickel thin film obtained.

The present international application claims priority from Japanese Patent Application No. 2016-166588 filed on Aug. 29, 2016, the full contents whereof are incorporated herein by reference.

The invention claimed is:

1. A method for manufacturing a thin film, comprising the steps of:
    introducing a vapor including a diazadienyl compound obtained by vaporizing a raw material for forming a thin film comprising the diazadienyl compound and a reactive gas into a film formation chamber in which a substrate is disposed, wherein the diazadienyl compound is represented by Formula (I) below:

wherein $R^1$ represents a $C_{1-6}$ linear or branched alkyl group, and M represents nickel atom or manganese atom; and forming, on a surface of the substrate, a thin film including at least one atom selected from nickel atom and manganese atom by inducing decomposition and/or chemical reaction of the diazadienyl compound.

2. The method for manufacturing a thin film according to claim 1, wherein the reactive gas is hydrogen.

3. The method for manufacturing a thin film according to claim 1, wherein $R^1$ in Formula (I) is a methyl group.

4. The method for manufacturing a thin film according to claim 3, wherein the reactive gas is hydrogen.

* * * * *